(12) United States Patent
Majidi et al.

(10) Patent No.: US 8,316,719 B2
(45) Date of Patent: Nov. 27, 2012

(54) STRETCHABLE TWO-DIMENSIONAL PRESSURE SENSOR

(75) Inventors: Carmel S. Majidi, Pittsburgh, PA (US);
Robert J. Wood, Cambridge, MA (US);
Phillippe Bérard, Lyssach (CH);
Yong-Lae Park, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 12/945,014

(22) Filed: Nov. 12, 2010

(65) Prior Publication Data

US 2012/0118066 A1 May 17, 2012

(51) Int. Cl.
*G01L 9/02* (2006.01)

(52) U.S. Cl. .............................. 73/719; 73/725; 73/734
(58) Field of Classification Search ............. 73/700–756
See application file for complete search history.

(56) References Cited

U.S. PATENT DOCUMENTS 3,304,528 A * 2/1967 Rastrelli et al. ................. 338/2
4,547,668 A * 10/1985 Tsikos ....................... 250/231.19
2008/0108122 A1* 5/2008 Paul et al. ..................... 435/183

* cited by examiner

*Primary Examiner* — Andre Allen
(74) *Attorney, Agent, or Firm* — Nixon Peabody LLP; David F. Crosby

(57) ABSTRACT

A pressure sensor for measuring the location and intensity of an applied pressure, including an elastomeric sheet; and a plurality of micro-channels embedded in the elastomeric sheet.

14 Claims, 6 Drawing Sheets

STRETCHABLE TWO-DIMENSIONAL PRESSURE SENSOR

GOVERNMENT LICENSE RIGHTS

This invention was made with government support under DMR-0820484, awarded by the National Science Foundation. The government has certain rights in this invention.

TECHNICAL FIELD

The invention relates generally to a sensing device and method for measuring applied pressures. More particularly, the invention relates to a device and method for measuring metrics of a sensing device having disclosed micro-structure embedded within prescribed material substrate.

BACKGROUND

Whitney first proposed embedding an elastomer with a conductive liquid for strain sensing. See, Whitney, R. J. "The measurement of changes in human limb-volume by means of a mercury-in-rubber strain gauge," *Proceedings of the Physiological Society* 109 5P-6P (1949). Whitney filled a rubber tube with mercury to measure the change in circumferential girth of a human limb. Sixteen years later, Rastrelli, Anderson, and Michie filed a patent application, that issued as U.S. Pat. No. 3,304,528, for a more general design for an elastomeric strain gauge that included a broad range of materials. In 2007, Cheng, Chao, and Cheung filed a patent application, that issued as U.S. Pat. No. 7,500,399, for a strain gauge containing doped polymeric fluid. A recent embodiment of the "Whitney" strain gauge is polydimethylsiloxane (PDMS) rubber embedded with a microchannel of eutectic, gallium indium (eGaIn) conductive liquid. See, Dickey, M. D., Chiechi, R. C., Larsen, R. J., Weiss, E. A., Weitz, D. A., and Whitesides, G. M. "Eutectic Gallium-Indium (EGaIn): A Liquid Metal Alloy for the Formation of Stable Structures in Microchannels at Room Temperature," *Advanced Functional Materials* 2008 1097-1104. See, also, Kim, H. J., Son, C., and Ziaie, B. "A multiaxial stretchable interconnect using liquid alloy-filled elastomeric microchannels," *Applied Physics Letters* 92 011904 (2008).

These strain gauges, however, can only sense extensional stretch, not transverse pressure. Additionally, existing pressure sensors and touch screens are composed of stiff, inorganic materials and polymers that limit flexibility and/or stretch, thus preventing biomechanical compatibility.

Emerging technologies, for example wearable computing, flexible tactile displays, and soft orthotics, may depend on stretchable sensors that register the location and intensity of pressure over a broad area. These "second skin" sensors are ideally conceived to maintain functionality even when stretched to several times their natural length. Additionally, they should also be soft enough to prevent significant interference with mechanics of human motion. Lastly, the sensors should be elastic and function repeatedly without hysteresis or permanent deformation.

SUMMARY

It is, therefore, an object of the present invention to overcome the deficiencies of the prior art to include a pressure sensor and method for measuring the location and intensity of an applied pressure including an elastomeric sheet, and a plurality of micro-channels embedded in the elastomeric sheet.

DETAILED DESCRIPTION OF EMBODIMENTS

Disclosed embodiments provide an elastomeric sheet embedded with a grid of conductive liquid channels configured to register the location and intensity of localized pressure. Embodiments may be useful for applications including stretchable tactile sensing for wearable computing and large-range pressure and motion sensing for soft orthotics. The geometry and spacing of conductive channels as well as the mechanical properties and thickness of the elastomeric matrix of embodiments may be configured according to desired sensor selectivity, range, and resolution.

Figure 1:
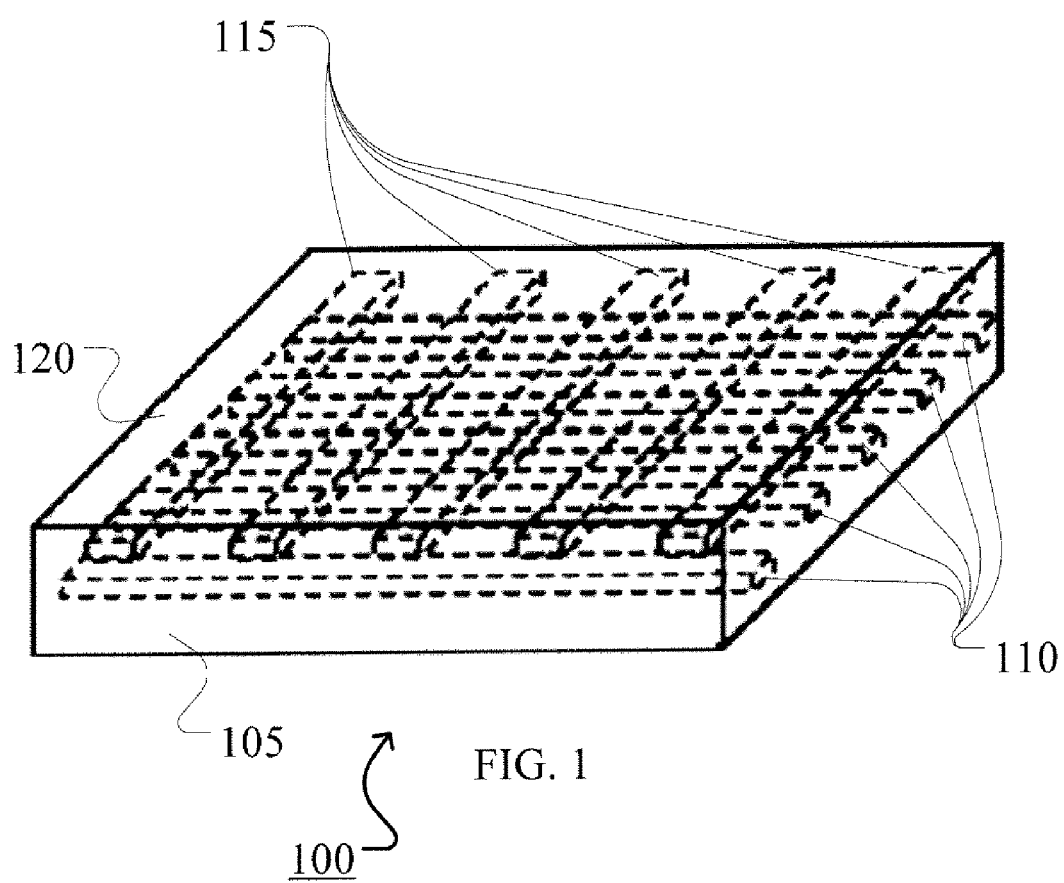
FIG. 1 illustrates a perspective view of an exemplary elastomeric sheet embedded with rows of perpendicularly aligned channels.

FIG. 1 illustrates a perspective view of an exemplary two-dimensional pressure sensor 100. Pressure sensor 100 includes an elastomeric sheet 105 embedded with substantially perpendicularly aligned channels 110 (e.g., microchannels) and channels 115 (e.g., micro-channels). Elastomeric sheet 105 may be a stretchable, soft (e.g., a softer-than-skin elastomeric sheet) elastomeric material, for example having a modulus of elasticity ranging from 10-1000 kiloPascals ("kPa"), for example about 100 kPa. Elastomeric sheet 105 may be composed of any elastomeric material, for example silicone, latex rubber, or polyurethane.

Channels 110 and 115 may contain conductive liquid, for example eutectic-Gallium Indium ("eGaIn"), mercury, carbon grease, or electrolytic fluid. The conductive liquid may have about one-tenth the conductivity of solid copper and aluminum. Hence, the conductive liquid filled channel may function as a highly stretchable electrical wire. Pressure on elastomeric sheet 105 at any point deforms the cross-section of nearby channels 110 and 115 comprising the grid, thus changing the electric resistance of the conductive liquid contained in one or more of channels 110 and 115. The location and intensity of the pressure may be computed by measuring the relative change in the electronic resistance of the conductive fluid in each of the channels 110 and 115 of the grid. The change in electronic resistance may be determined by conventional resistance measuring devices, for example an ohmmeter or Wheatstone bridge. In this fashion, pressure sensor 100 is configured to sense the location and intensity of pressure over the entire two-dimensional surface 120 (or the opposing surface which is not shown).

Sensitivity to pressure and stretch are decoupled by selecting the appropriate channel geometry. Sensor decoupling may allow for determining whether the change in the conductivity of conductive fluid filling a channel is induced by pressure or stretching of the elastomeric sheet. Design rules based on experimentally-verified insights are derived from theories of continuum mechanics and linear elastic fracture mechanics ("LEFM"). The pressure sensitivity of a pressure sensor may be dependent on both the distance of an embedded channel from the surface of the elastomeric sheet and the aspect ratio of the channel cross-section. In contrast, stretching sensitivity may be invariant to both of these values.

The mathematical relationship between electrical resistance and both stretch and pressure may be established with theories of continuum mechanics and LEFM. Pressure sensors according to embodiments disclosed herein, thus, may obey a mathematical model that is algebraic, closed-form, and predictive. Therefore, an accurate estimate of the change in electrical resistance for a prescribed pressure or stretch may be established with theory alone and without data-fitting or experimental measures.

In the case of pure stretching, the change in electrical resistance may be determined by the equation:

$$\frac{\Delta R}{R_0} = \lambda^2 - 1 \quad (1)$$

where $R_0$ is the natural (unstretched) resistance of the conductive fluid filling a channel, $\Delta R$ is the change in resistance of the conductive fluid filling a channel, and $\lambda$ is equal to the stretched length divided by the natural length. For example, a stretching strain of 400% corresponds to $\lambda=5$ (i.e., the final length is five times the initial length), so the electrical resistance increases by a factor of 25, or 2400%. Alternatively, a strain of 10% ($\lambda=1.1$) corresponds to a 1% increase in resistance, which may be measured with a precision ohmmeter or a Wheatstone bridge with a differential amplifier.

The mechanics of pressure sensing may also be approximated with an algebraic formula:

$$\frac{\Delta R}{R_0} = \frac{1}{1 - 3w\chi p/2hE} - 1 \quad (2)$$

where h and w are the thickness and width of the channel, respectively, E is the elastic modulus of the elastomeric sheet, and p is the magnitude of the surface pressure. The constant $\chi$ is a unitless parameter that depends on the width a over which pressure is applied, the vertical distance z of the micro-channel from the surface of the elastomeric sheet, and the horizontal distance x of the center of pressure from the centerline of the micro-channel:

$$\chi = \frac{\left\{\tan^{-1}\left(\frac{a+2x}{2z}\right) + \tan^{-1}\left(\frac{a-2x}{2z}\right)\right\} \begin{pmatrix} -8x^2a^2 + 32x^2z^2 + 8z^2a^2 + \\ 16x^4 + 16z^4 + a^4 \end{pmatrix} - 16zax^2 + 4za^3 + 16z^3a}{(\pi(4x^2 + 4xa + a^2 + 4z^2)(4x^2 - 4xa + a^2 + 4z^2))} \quad (3)$$

In formula (3), the parameter $\chi$ equals one when both x and z are small compared to a. This corresponds to the condition when a micro-channel is immediately beneath an area of applied pressure. Sensitivity to pressure may be almost entirely lost (i.e., $\chi \approx 0$) when either x or z is greater than or equal to a. These trends imply that channels for pressure sensing must be embedded near the surface of the elastomeric sheet and that the channels will only register surface pressures that act immediately above the channel.

Equation (2) above implies that the sensitivity to pressure is greatest when the anticipated pressure p is large compared to the ratio 2hE/3w. In other words, pressure sensitivity is greatest for channels that have a low aspect ratio cross-section (h<<w) and are surrounded by a soft elastomeric material (E~0.1-1 megaPascals ("MPa"), 1 MPA=$10^6$ Newtons/meters).

For example, a softer-than-skin elastomeric sheet with an elastic modulus E=0.1 MPa may be embedded with a micro-channel of width w=100 microns and thickness h=20 microns. In response to a typical keystroke pressure in the range of 1-10 kPa, the electrical resistance of the embedded conductive fluid filling the micro-channel would change on the order of 1%. In contrast, peak pressure in foot-ground contact during walking are on the order of 100 kPa, which would result in a ~50% change in electrical resistance. For an embodiment, design parameters h, w, and E may be selected such that 2hE/3w is comparable to the range of anticipated values for p.

Because pressure sensors according to such embodiments are composed entirely of soft elastomer and liquid, such pressure sensors may remain functional even when substantially stretched, for example by as much as 500%. Moreover, because of the low stiffness of such pressure sensors, embodiments may be mechanically compatible with natural human motion.

Figure 2:
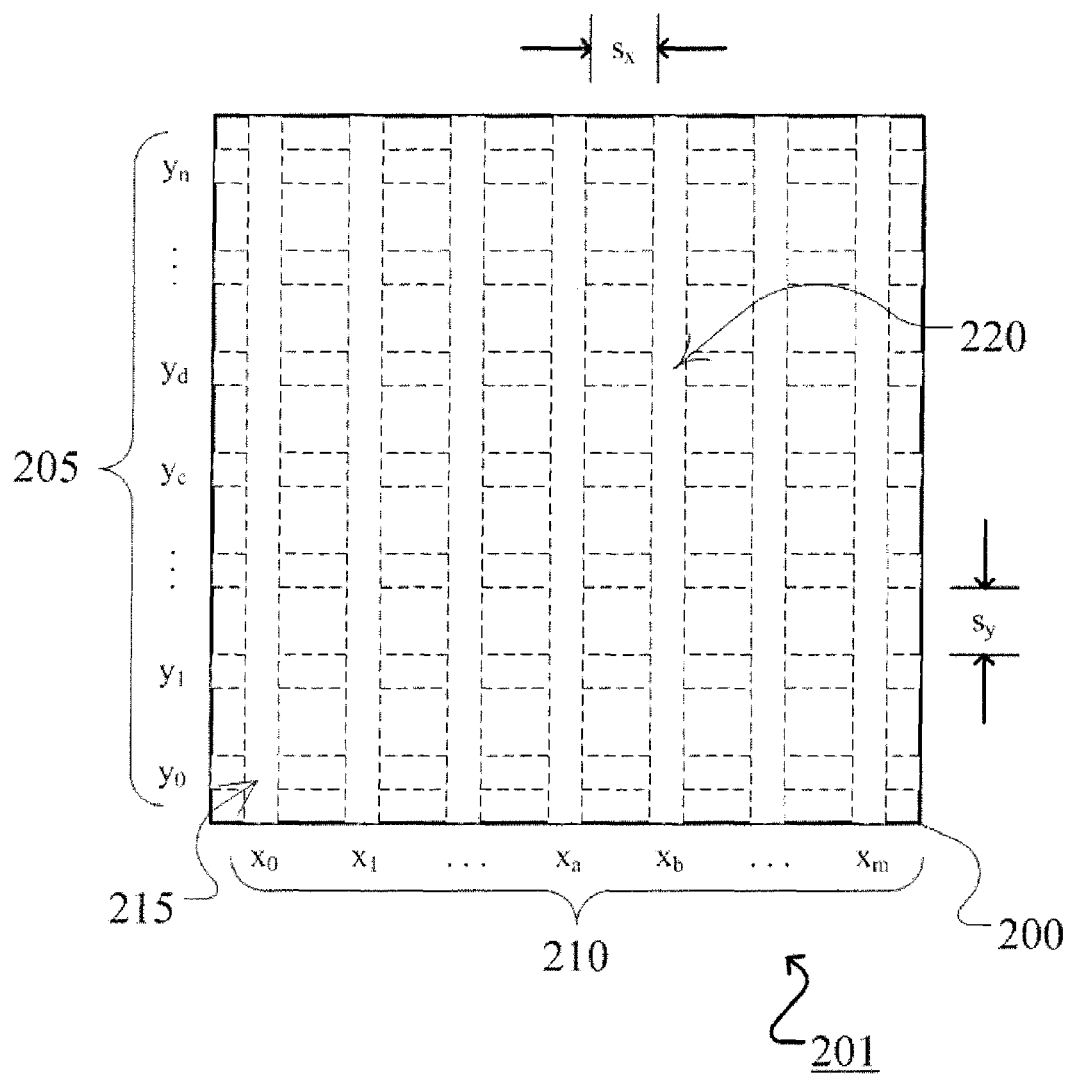
FIG. 2 illustrates a conceptual view of an exemplary elastomeric sheet embedded with rows of perpendicularly aligned channels.

Referring now to FIG. 2, a conceptual view of an exemplary elastomeric sheet 200 is embedded with substantially perpendicularly aligned horizontally oriented channels 205 (labeled $y_0, y_1, \ldots, y_n$) and vertically oriented channels 210 (labeled $x_0, x_1, \ldots, x_m$). Thus, horizontally oriented channels 205 and vertically oriented channels 210 form a grid. Points on elastomeric sheet 200 may be referred to by their horizontal and vertical coordinates (i.e., their (x, y) coordinates). For example, point 215 may be referred to as point (0, 0) and point 220 may be referred to as $(x_b, y_d)$. Receiving pressure on elastomeric sheet 200 at any point (x, y), thus, changes the electric resistance of a conductive fluid contained in nearby channels. For example, pressure near point 220 may change the electric resistance of the conductive fluid filling nearby channels $x_a$, $x_b$, $y_c$, and $y_d$. The indices {a, b} and {c, d} correspond to the lower and upper rounded values of $x/s_x$ and $y/s_y$, respectively, where $s_x$ is the channel spacing along the x-direction and $s_y$ is the channel spacing along the y-direction. For example, $s_x$ and $s_y$ may be between 1 micron and 10 millimeters. Conversely, measuring a relative increase in electric resistance along channels $x_p$ and $y_q$ implies that pressure is applied at the coordinates (ps, qs).

The thickness and elastic stiffness of elastomeric sheet 200 and the cross-sectional dimensions of the channels 205 and 210 may determine the minimum pressure needed to produce a measurable change in electrical resistance of the conductive fluid filling channels 205 and 210. The minimum measureable pressure may also be related to the sensitivity of the ohmmeter (not shown in FIG. 2) used to measure electrical resistance of the conductive fluid filling channels 205 and 210.

Channel spacing may influence the deformation and transfer of stress throughout elastomeric sheet 200 and, therefore, may influence the pressure sensitivity and bandwidth of the pressure sensor. However, channel spacing may have a greater impact on the spatial resolution of the sensor.

Additionally, viscosity of the conductive liquid used to fill the channels and the viscoelasticity of the elastomeric sheet may be chosen to achieve a desired relaxation time. Both the elastomeric sheet and conductive liquid may be chosen to have as low a viscosity as possible, thus achieving a minimal relaxation time which may be desirable for certain applications. This relaxation time is on the order of $\eta/E$, where $\eta$ is the coefficient of viscosity and E is the elastic modulus of the elastomer sheet. Elastomers with $\eta$ on the order of 100 to 105 Pascal-seconds and E on the order of 100 to 1000 kiloPascals will relax within a fraction of a second.

Figure 3:
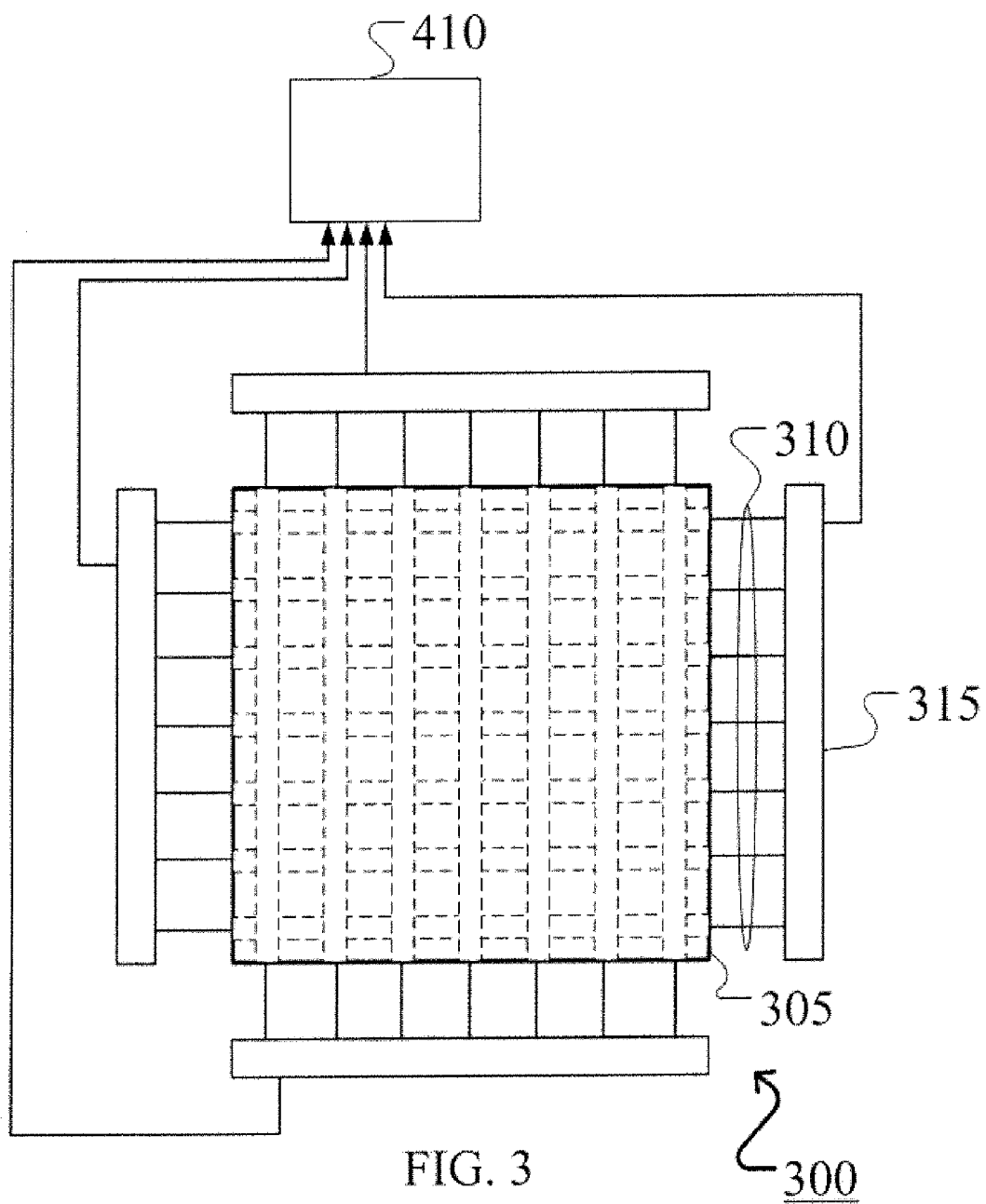
FIG. 3 illustrates a conceptual view of an exemplary system for detecting the location and intensity of pressure over a two-dimensional surface.

Referring now to FIG. 3, a conceptual view of an exemplary system 300 for detecting the location and intensity of pressure over a two-dimensional surface is shown. System 300 includes a pressure sensor 305, for example the pressure sensor 100 of FIG. 1 or pressure sensor 201 of FIG. 2. System 300 also includes one or more ohmmeter 315 operatively coupled via leads 310 (e.g., wires) to the conductive fluid contained in channels embedded in pressure sensor 305. Of course, while FIG. 3 illustrates 4 independent ohmmeters 315, one of ordinary skill in the art understands that greater or fewer ohmmeters 315 may be implemented as long as the electric resistivity of the conductive fluid in each channel is measured. Ohmmeter 315 is configured to measure the electric resistance of the conductive fluid in each channel embedded in pressure sensor 305 and output a signal indicating either the electric resistance or the relative change in electric resistance in each channel's conductive fluid. For example, ohmmeter 315 may output a signal to a computing device 410 configured to compute the intensity and location of pressure received by pressure sensor 305 in response to data including the electric resistance or change in electric resistance of the conductive fluid in each channel embedded in pressure sensor 305. Of course, in other embodiments, ohmmeter 315 may directly output, for example to a display device, printer, or other device, electric resistance or change in electrical resistance of the conductive fluid in each channel embedded in pressure sensor 305.

Figure 4:
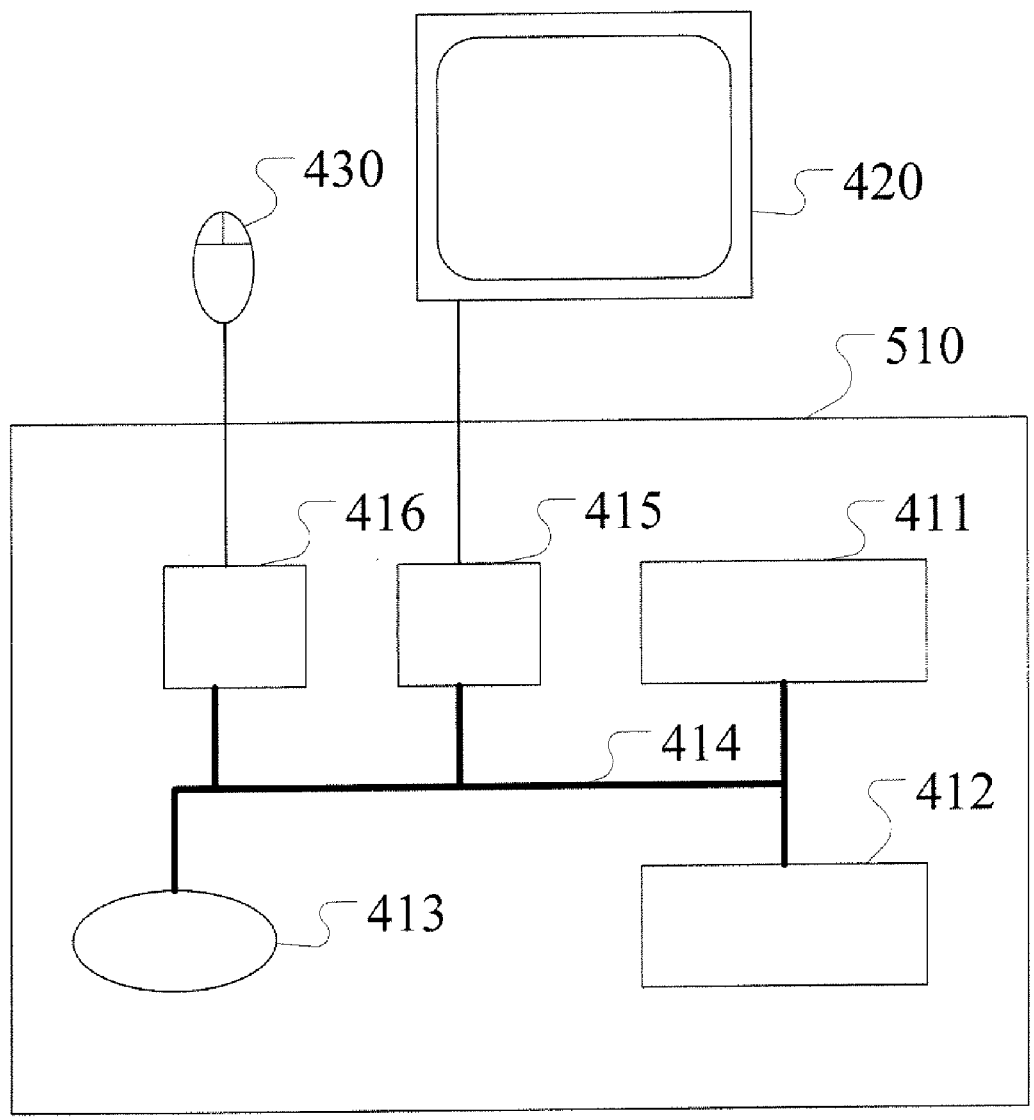
FIG. 4 illustrates an exemplary computing device useful for computing the location and intensity of pressure over an exemplary pressure sensor.

FIG. 4 illustrates a computing device 410 useful for computing the location and intensity of pressure over a pressure sensor, for example pressure sensor 305 of FIG. 3. Computing device 410 has one or more processing device 411 designed to process instructions, for example computer readable instructions stored on a storage device 413. By processing instructions, processing device 411 may render on a display device 420, for example a display showing the location and intensity of pressure received on a pressure sensor. Storage device 413 may be any type of storage device (e.g., an optical storage device, a magnetic storage device, a solid state storage device, etc.), for example a non-transitory storage device. Alternatively, instructions may be stored in remote storage devices, for example storage devices accessed over a network or the Internet. Computing device 410 additionally has memory 412, an input controller 416, and an output controller 415. A bus 414 operatively couples components of computing device 410, including processing device 411, memory 412, storage device 413, input controller 416, output controller 415, and any other devices (e.g., network controllers, sound controllers, etc.). Output controller 415 may be operatively coupled (e.g., via a wired or wireless connection) to a display device 420 (e.g., a monitor, television, mobile device screen, etc.) in such a fashion that processing device 411 and output controller 415 can transform the display on display device 420 (e.g., in response to modules executed). Input controller 416 may be operatively coupled (e.g., via a wired or wireless connection) to one or more input device 430 (e.g., mouse, keyboard, touch-pad, scroll-ball, touch-display, etc.) in such a fashion that input can be received from a user. Additionally, input controller 416 and/or output controller 415 may be operatively coupled to one or more ohmmeters (e.g., ohmmeter 315 shown in FIG. 3) to receive as input signals indicating the electric resistance or change in electric resistance of conductive fluid in each channel of a pressure sensor (e.g., pressure sensor 305 of FIG. 3).

Of course, FIG. 4 illustrates computing device 410, display device 420, and input device 430 as separate devices for ease of identification only. Computing device 410, display device 420, and input device 430 may be separate devices (e.g., a personal computer connected by wires to a monitor and mouse), may be integrated in a single device (e.g., a mobile device with a touch-display, such as a smartphone or a tablet, or a wearable device), or any combination of devices (e.g., a computing device operatively coupled to a touch-screen display device, a plurality of computing devices attached to a single display device and input device, etc.). Additionally, a computing device 410 may not be operatively coupled to a display device 420 or an input device 430, but rather may be operatively coupled to other computing devices, for example computing devices in part of a system for wearable computing, soft orthotics, or biomechanical monitoring. Further, while computing device 410 is shown as a single, discrete device, computing device 410 may be multiple computing devices coupled (e.g., networked) together, for example a cloud computing system or a clustered server.

Embodiments may include software configured for computing the intensity and location of pressure received by a pressure sensor, for example pressure sensor 305 of FIG. 3. For example, computer-readable instructions may be stored on non-transitory storage device 413. The computer-readable instructions may be configured to be processed by processing device 411 to receive a first set of signals from one or more ohmmeter indicating the electric resistance of conductive fluid filling each of a plurality of channels in a pressure sensor, to receive a second set of signals from the ohmmeter indicating the electric resistance of the conductive fluid filling each of the plurality of channels in the pressure sensor, compute a difference in electric resistance of the conductive fluid filling each of the plurality of channels in the pressure sensor, compute the intensity and location of pressure received by the pressure sensor, and output signals including the intensity and location of pressure received by the pressure sensor. The output may be to a display device or to a further computing device for example.

Figure 5A:
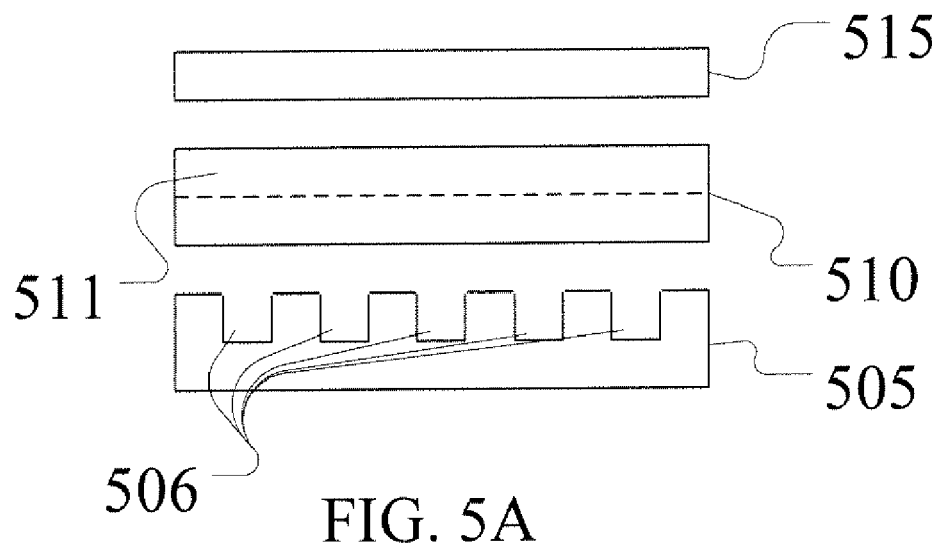
FIG. 5A illustrates a cross-sectional view of three elastomeric sheets useful for fabricating an exemplary pressure sensor.

Referring now to FIG. 5A, a cross-sectional view of three elastomeric sheets 505, 510, and 515 useful for fabricating an exemplary pressure sensor is shown. Sheet 515 may be a substantially flat sheet. Sheet 510 may contain open channels 511 (only one of which may be viewed in FIG. 5A) and sheet 505 may contain open channels 506. Characteristics of channels 511 and 506, as well as dimensions of sheets 505, 510, and 515, may be chosen according to a desired sensor sensitivity, range, and resolution. Sheets 510 and 505 may, for example, be identically formed but may be oriented such that open channels 506 and open channels 511 are perpendicular to each other. Sheets 505, 510, and 515 may be formed in conventional fashion, for example molds may be micromachined, printed, or milled from an inorganic solid or polymer and an elastomer may be cast into the mold, cured, and then released. Uncured elastomeric material (e.g., silicone rubber) may be poured into the mold, cured, for example at room temperature or under moderate heat (e.g., 60-100° Celsius).

Figure 5B:
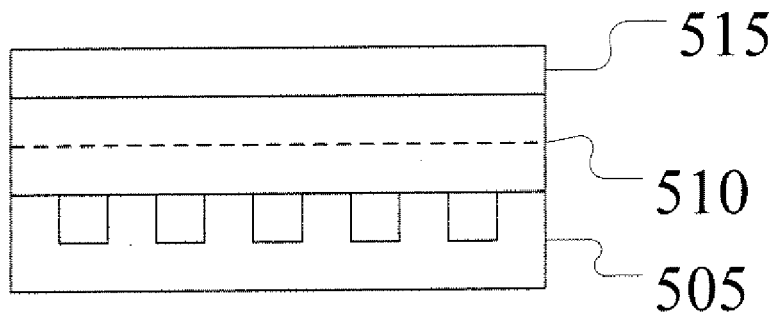
FIG. 5B illustrates a cross-sectional view three elastomeric sheets bonded together useful for fabricating an exemplary pressure sensor.
Figure 5C:
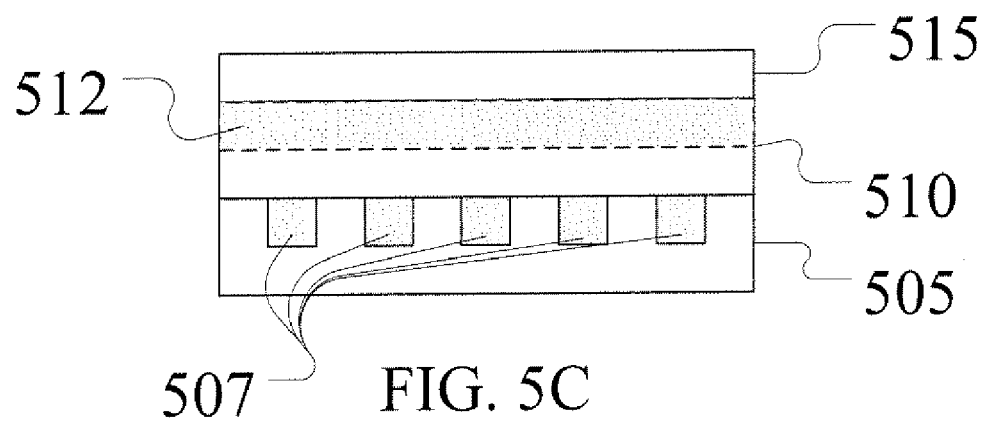
FIG. 5C illustrates a cross-sectional view of three elastomeric sheets bonded together having channels filled with conductive liquid useful for fabricating an exemplary pressure sensor.

Referring to FIG. 5B, a cross-sectional view of the three elastomeric sheets 505, 510, and 515 of FIG. 5A are shown bonded together. The elastomeric sheets may be bonded together, for example, with an elastomer. The elastomeric sheets may be bonded together, for example, by spin coating uncured rubber on a silicon wafer, coating the smooth side of each layer by wiping it on the wafer, stacking the layers, and then curing the composite. After sheets 505, 510, and 515 are bonded together, channels 506 and 511 may be filled with a conductive liquid in conventional fashion, for example by injecting conductive liquid into the channel from one or both open ends of the channel with a syringe.

Figure 6A:
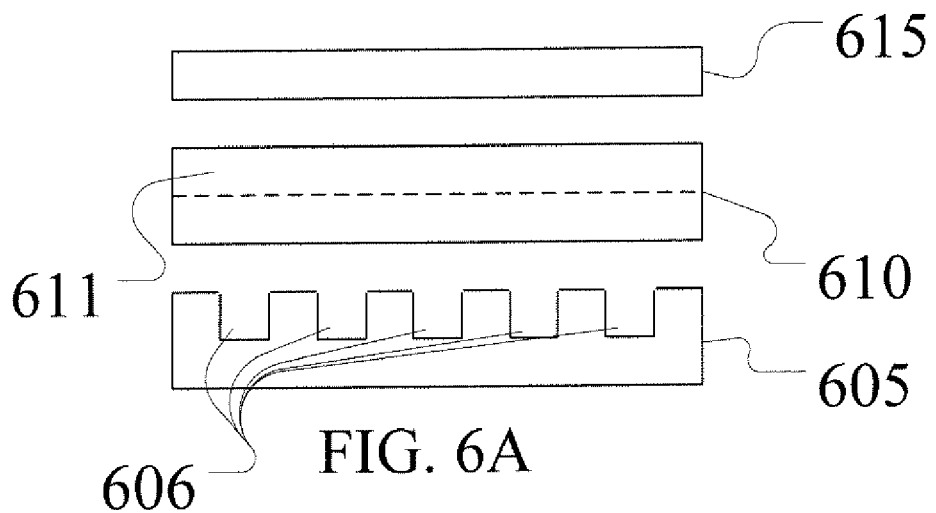
FIG. 6A illustrates a cross-sectional view of three elastomeric sheets useful for fabricating an exemplary pressure sensor.
Figure 6B:
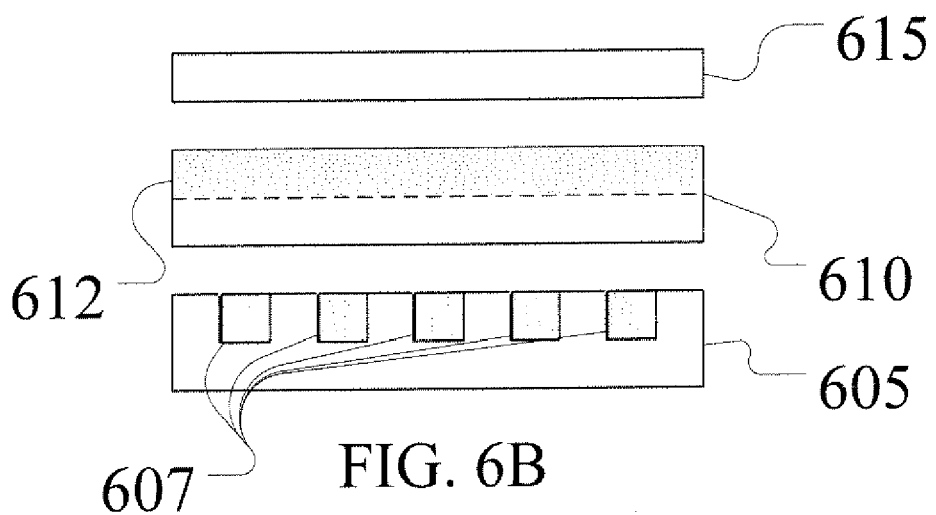
FIG. 6B illustrates a cross-sectional view three elastomeric sheets having channels filled with conductive liquid useful for fabricating an exemplary pressure sensor.
Figure 6C:
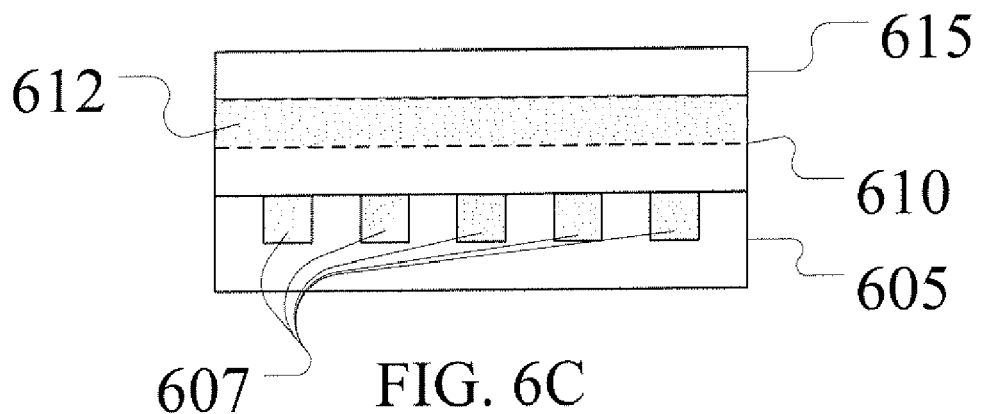
FIG. 6C illustrates a cross-sectional view of three elastomeric sheets bonded together having channels filled with conductive liquid useful for fabricating an exemplary pressure sensor.

Of course, pressure sensors according to embodiments disclosed herein may be fabricated in other ways. For example, the open channels may be filed with a conductive liquid before the layers are bonded. Referring to FIG. 6A, an elastomer may be molded into three sheets in similar fashion to FIG. 5A. Referring to FIG. 6B, an entire surface of each of sheets 605 and 610, including channels 606 and 611, may be covered with a conductive liquid 607 and 612. Excess conducive liquid 607 and 612 (i.e., liquid outside of channels 606 and 611) may be removed, for example by brushing or through repeated adhesion to a sticky surface. Once channels 606 and 611 are filled with conductive fluid 607 and 612, sheets 605, 610, and 615 may be bonded together. FIG. 6C illustrates a pressure sensor having sheets 605, 610, and 615 bonded together in which embedded perpendicular channels 606 and 611 are filled with conductive fluid 607 and 612.

Of course, while FIGS. 5A through 6C illustrate elastomeric sheets having only five channels, one of ordinary skill in the art understands that these illustrations are for explanation only and that an elastomeric sheet according to embodiments may have any dimensions and any number of channels embedded therein.

The size of channels of a pressure sensor, for example channels 606 and 611 shown in FIG. 6A, may be controlled by the geometry of the mold used for casting the elastomeric sheets, for example elastomeric sheets 605 and 610 shown in FIG. 6A. For high resolution sensing with distinct pressure measurements spaced 1 to 1000 microns apart, the channels should be from 1 to 1000 microns in width and depth. Increasing the ratio of width to depth improves pressure sensitivity. The ratio may be selected to be greater than 1 to provide a high resolution. Photolithographic processing may be required for pressure sensors having cross-sectional dimensions of less than 250 microns.

While embodiments disclosed herein refer to detecting the location and intensity of pressure received on a surface of a pressure sensor, one of ordinary skill in the art understands that embodiments may detect the location and intensity of multiple points of pressure on a surface or varying degrees of pressure across the entire surface of a pressure sensor.

Additionally, while channels illustrated in embodiments herein appear to generally have rectangular cross-sections, alternative shaped cross-sections may be used. Moreover, embodiments shown herein illustrate channels having a substantially perpendicular alignment. Of course, alternative embodiments may have grids of channels embedded in elastomeric sheets crossing at alternative angles, for example in a pattern forming diamonds rather than squares. In still other embodiments, more than two sets of channels may be embedded in an elastomeric sheet. For example, embodiments may have three sets of channels, each oriented at a sixty degree offset, thus creating a grid of equilateral triangles.

Pressure sensors according to embodiments disclosed herein have many potential applications. For example, such pressure sensors may sense foot contact and pressure in soft orthotic insoles. Electromechanically active insoles and orthotic sleeves rely on hyperelastic pressure sensing in order to determine the appropriate stimulation needed to improve stance stability or gait locomotion in patients with brain injury or degraded motor control. Such sensors should be softer than skin in order to avoid altering the natural mechanics of the foot or joint.

In addition to medical orthoses, hyperelastic pressure and stretch sensing can be used to monitor motion and contact during athletic activity. Because pressure sensors according to embodiments disclosed herein are soft and durable, they can remain functional under a broad range of loading and impact conditions and not interfere with the natural mechanics of the athlete. Pressure sensing is particularly important for monitoring impact pressures in both foot-ground and ball-body contact. Stretch sensing can be used to monitor limb extension and cardiovascular chest expansion.

Further, pressure sensors according to embodiments disclosed herein may be useful for tactile sensing for stretchable touch screens and wearable electronics. Flexible electronics and rollable computer displays represent preliminary efforts towards fully functional stretchable and wearable computers that can radically change their form factor and conform to human morphology and motion. A stretchable keyboard may be accomplished with a cross-grid of conductive fluid microchannels embedded in a silicone rubber sheet. The location of a key stroke may be registered by the pair of intersecting channels that produce the greatest change in electrical conductivity.

Of course, these are only exemplary applications of embodiments of pressure sensors disclosed herein. One of ordinary skill in the art understands that such pressure sensors may be useful for a broad range of other applications. While the stretchable pressure sensor is described herein by way of example and embodiments, those skilled in the art will recognize that the pressure sensor and method of fabricating the pressure sensor is not limited to the embodiments or drawings described. It should be understood that the drawings and description are not intended to limit embodiments to the particular form disclosed. Rather, the intention is to cover all modifications, equivalents and alternatives falling within the spirit and scope of the invention defined by the appended claims. Any headings used herein are for organizational purposes only and are not meant to limit the scope of the description or the claims. As used herein, the word "may" is used in a permissive sense (i.e., meaning having the potential to), rather than the mandatory sense (i.e., meaning must). Similarly, the words "include", "including", and "includes" mean including, but not limited to.

The invention has been described through embodiments. However, various modifications can be made without departing from the scope of the invention as defined by the appended claims and legal equivalents.

What is claimed is:

1. A pressure sensor for measuring the location and intensity of an applied pressure, comprising:

an elastomeric sheet; and a plurality of micro-channels embedded in said elastomeric sheet;

wherein said micro-channels are filled with an electrically conductive material.

2. The pressure sensor of claim 1, wherein said micro-channels comprise two orthogonal sets of rows.

3. The pressure sensor of claim 1, wherein said elastomeric sheet is an elastic material with an elastic modulus of 10-1000 kiloPascals.

4. The pressure sensor of claim 1, wherein each of said micro-channels has a width greater than or equal to a depth.

5. The pressure sensor of claim 4, wherein said width and said depth are each between 1 and 1000 microns in length.

6. The pressure sensor of claim 5, wherein said micro-channels comprise two orthogonal sets of rows with a spacing between parallel rows in each set, and wherein said spacing is between 1 micron and 10 millimeters.

7. A method of fabricating a pressure sensor comprising:

forming an elastomeric sheet having a plurality of micro-channels embedded therein; and filling said micro-channels with a conductive material.

8. The method of claim 7, wherein said forming step comprises:

casting an elastomeric material in each of three molds to form a flat elastomeric sheet and two micro-channeled elastomeric sheets;

bonding the flat elastomeric sheet and the two micro-channeled elastomeric sheets.

9. The method of claim 8, wherein said filling step occurs between said casting step and said bonding step.

10. The method of claim 8, wherein said filling step occurs after said forming step.

11. A method of determining a location of pressure applied to a pressure sensor, comprising:

measuring at a first time the electric resistance of a conductive fluid filling each of a plurality of channels embedded in said pressure sensor;

measuring at a second time the electric resistance of said conductive fluid filling each of said plurality of channels embedded in said pressure sensor;

identifying the channels having the greatest change in electric resistance.

12. A method of determining an intensity of pressure applied to a pressure sensor, comprising:

measuring at a first time the electric resistance of a conductive fluid filling each of a plurality of channels embedded in said pressure sensor;

measuring at a second time the electric resistance of said conductive fluid filling each of said plurality of channels embedded in said pressure sensor;

determining a relative change in the electrical resistance of each of said channels.

13. A pressure sensor capable of indicating intensity and location of an applied pressure, comprising:

an elastomeric sheet defining a two dimensional surface;

a first plurality of micro-channels, embedded in said elastomeric sheet, extending along the two dimensional surface and a second plurality of micro-channels, embedded in said elastomeric sheet, extending along the two dimensional surface transverse to but not intersecting the first plurality of micro-channels;

an electrically conductive liquid filling at least one of the first plurality of micro-channels and at least one of the second plurality of micro-channels; and wherein the first plurality of micro-channels do not intersect with the second plurality of micro-channels and the electrically conductive fluid filling at least one of the first plurality of micro-channels does not come in contact with the electrically conductive fluid filling at least one of the second plurality of micro-channels.

14. A pressure sensor according to claim 13 wherein a pressure applied to the two dimensional surface causes at least one of the first plurality of micro-channels and the second plurality of micro-channels to change in shape and cause a conductive liquid in the micro-channel to change in resistance.

* * * * *